United States Patent [19]

Yabe

[11] Patent Number: 4,786,965
[45] Date of Patent: Nov. 22, 1988

[54] ELETRONIC ENDOSCOPE WITH AN IMAGING DEVICE HAVING SIDE BONDING PADS

[75] Inventor: Hisao Yabe, Hachioji, Japan

[73] Assignee: Olympus Optical Co., Ltd., Tokyo, Japan

[21] Appl. No.: 83,401

[22] Filed: Aug. 10, 1987

[30] Foreign Application Priority Data

Sep. 4, 1986 [JP] Japan ................... 61-209155

[51] Int. Cl.⁴ .................. H04N 7/18; H04N 3/14
[52] U.S. Cl. .................. 358/98; 358/213.11; 128/4; 357/80
[58] Field of Search .............. 388/38, 213.11, 229; 128/4, 6; 357/74, 80

[56] References Cited

U.S. PATENT DOCUMENTS

| | | | |
|---|---|---|---|
| 4,442,456 | 4/1984 | Uwata et al. | 358/213.11 |
| 4,477,828 | 10/1984 | Scherer | 357/80 |
| 4,491,865 | 1/1985 | Danna et al. | 358/98 |
| 4,573,450 | 3/1986 | Arakawa | 358/98 |
| 4,594,613 | 6/1986 | Shinbori et al. | 358/213.11 |
| 4,622,954 | 11/1986 | Arakawa et al. | 358/98 |
| 4,677,471 | 6/1987 | Takamura et al. | 358/98 |
| 4,682,219 | 7/1987 | Arakawa | 358/98 |
| 4,706,654 | 11/1987 | Giu et al. | 128/4 |

Primary Examiner—James J. Groody
Assistant Examiner—John K. Peng
Attorney, Agent, or Firm—Armstrong, Nikaido, Marmelstein & Kubovcik

[57] ABSTRACT

An electronic endoscope, equipped with an imaging apparatus having side bonding pads, is provided with a flexible insertable part which is formed to be small in diameter. Within a tip of the insertable part, a solid state imaging device is formed and a solid state imaging chip is provided with chip side bonding pads. The solid state imaging chip is secured to a base provided with base side bonding pads in groups. The chip side bonding pads and base side bonding pads are connected respectively with each other through bonding wires. The chip side bonding pads are provided on one side of the image area in a plurality of rows.

18 Claims, 4 Drawing Sheets

ELETRONIC ENDOSCOPE WITH AN IMAGING DEVICE HAVING SIDE BONDING PADS

FIELD OF THE INVENTION

This invention relates to an electronic endoscope wherein the diameter of the insertable part can be made smaller.

BACKGROUND OF THE INVENTION AND RELATED ART STATEMENT

Various endoscopes (which shall be called electronic endoscopes in the present invention) wherein solid state imaging devices, such as charged coupled devices (CCD's), are used for an imaging means have been recently suggested.

Such an electronic endoscope has advantages in that it has a higher resolving degree than a fiberscope, it can easily record and reproduce picture images and it can easily make picture image processes such as the magnification of picture images and comparison of two picture surfaces.

The above mentioned electronic endoscope is desired to be thin in the insertable part in order to reduce the pain to the patient when it is inserted. However, the outside diameter of this insertable part or particularly of the tip is restricted by the size and shape of a solid state imaging device internally provided in the tip.

In a conventional solid state imaging device, for example, as shown in the specification of U.S. Pat. No. 4,491,865, a solid state imaging chip is secured on a base. On the solid state imaging chip, chip side bonding pads are provided on the periphery of a square or rectangular image area (effective imaging part). On the other hand, on the base side, base side bonding pads (leads) are provided. The above mentioned chip side bonding pads and base side bonding pads are connected respectively with each other through bonding wires or the like. The number of leads provided on the above mentioned base is at least 6 but is generally 14 to 20. For example, respectively 10 of the above mentioned chip side and base side bonding pads are arranged generally along the two opposed sides of the above mentioned image area.

In case the bonding wire is, for example, a general gold (Au) wire or aluminum (Al) wire of 25 μm., the size of the above mentioned chip side bonding pad may be about 0.1 to 0.12 mm. square, the spacing may be about 0.1 mm. and therefore the pitch may be about 0.2 mm. On the other hand, in the above mentioned base side bonding pads, as the base is made of ceramics, glass epoxy or a lead frame, the pitch of the pads must be about 0.635 mm. (1/40 inch). Therefore, whether these base side bonding pads can be laid out at high space efficiency influences the outside diameter of the insertable parts.

However, conventionally, the above mentioned base side bonding pads have been arranged in a row along the side of the imaging chip. Therefore, there are problems that the pitch of the above mentioned base side bonding pads is so large that, particularly, in case there are many leads, the base will become large and, as a result, the insertable part of the electronic endoscope will become thick.

When the chip side bonding pads are provided, along the two sides opposed to each other on the image area, the chip itself will become larger than when they are collected on one side and, as a result, the diameter of the insertable part will become even larger.

OBJECTS AND SUMMARY OF THE INVENTION

An object of the present invention is to provide an electronic endoscope wherein the solid state imaging device can be made small or in the form desirable to be made small in diameter in layout and the insertable part can be made smaller in diameter.

In the present invention, a solid state imaging device is provided in a space enclosed with an insertable part tip inside diameter and contents and base side bonding pads are arranged in groups.

Other features and advantages of the present invention will become apparent enough with the following explanation.

BRIEF DESCRIPTION OF THE DRAWINGS

FIG. 1 is an explanatory view showing an entire electronic endoscope.

FIG. 2 is a cross-sectioned view of a tip of the insertable part of the electronic endoscope.

FIG. 3 is a sectioned view of a solid state imaging device.

FIG. 4 is a sectioned view on line A—A' in FIG. 2.

FIG. 5 is an explanatory view showing the formation of the electronic endoscope.

FIG. 6 is a cross-sectioned view of a tip of the insertable part of an electronic endoscope.

FIG. 7 is a sectioned view in the direction B—B' in FIG. 6.

DETAILED DESCRIPTION OF PREFERRED EMBODIMENTS

The present invention shall be explained in detail in the following with reference to the drawings.

Figure 1:
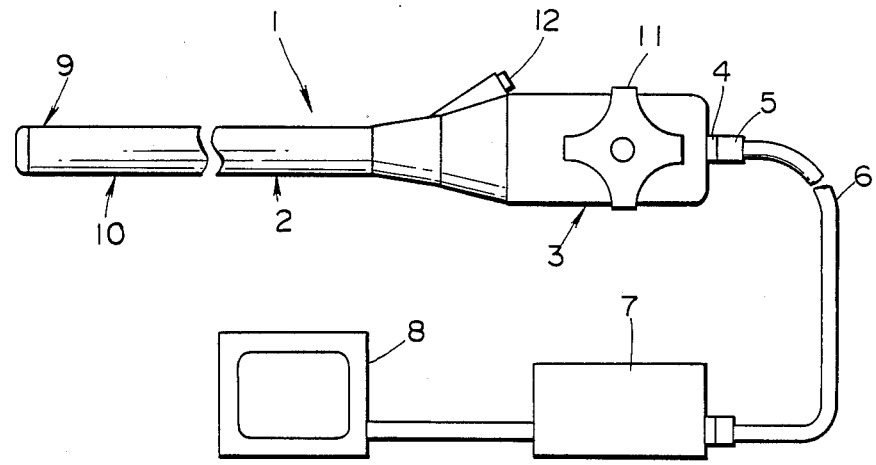
FIGS. 1 to 5 relate to the first embodiment of the present invention.

As shown in FIG. 1, in an electronic endoscope 1, a thick operating part 3 is connected to the rear end of an elongated and, for example, flexible insertable part 2. A connector receiver 4 is provided at the rear end of the above mentioned operating part 3. The above mentioned operating part 3 and a controlling part 7 containing a light source device and a video processing part are to be connected with each other through a cable 6 having a connector 5 to be fitted to the connector receiver 4. A color CRT monitor 8, as a displaying means is to be connected to the above mentioned controlling device 7.

A rigid tip 9 and a curvable part 10, curvable rearward and adjacent to the tip 9, are provided in turn on the tip side of the above mentioned insertable part 2. Also, by rotating and operating a curving operation knob 11, provided on the above mentioned operating part 3, the above mentioned curvable part 10 can be curved horizontally and vertically. An inserting port 12 communicating with a forceps channel provided within the above mentioned insertable part 2 is provided in the above mentioned operating part 3.

Figure 2:
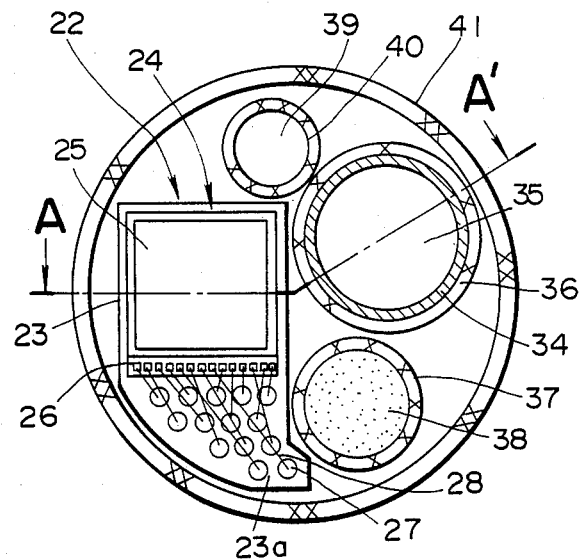
Figure 3:
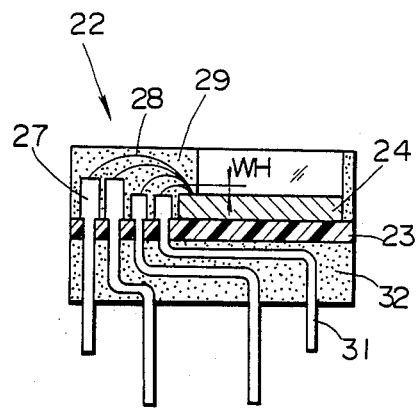
Figure 4:
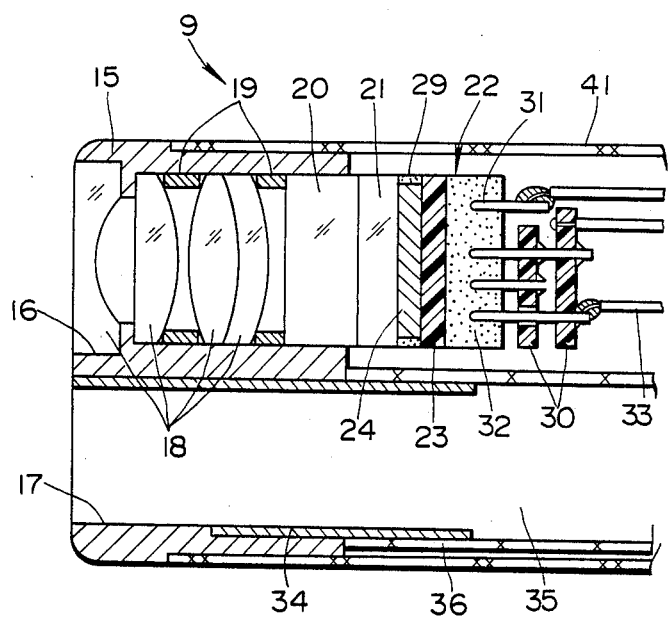

The above mentioned tip 9 is formed as shown in FIGS. 2 to 4.

The tip 9 is provided with a substantially columnar tip body 15 made of rigid material such as a metal. An observing through hole 16 passing parallelly with the lengthwise direction of the above mentioned insertable part 2 and a forceps channel through hole 17 and an illuminating through hole and an air and water feeding channel through hole not illustrated are formed in the tip body 15.

Figure 5:
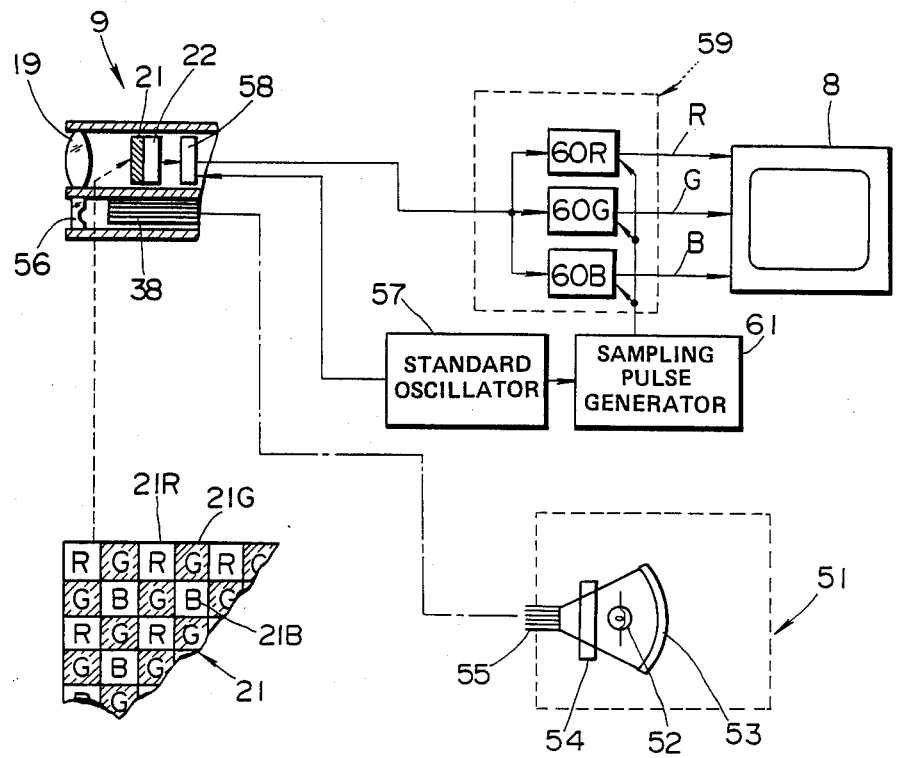

An objective system 18 is positioned by a positioning member 19 and is fitted in the above mentioned observing through hole 16. A device supporting optical member 20 is fitted to the rear end of the observing through hole 16. A color filter array 21 is secured to the rear end of the device supporting optical member 20. A solid state imaging device 22 is secured to the rear end of the color filter array 21. In the above mentioned color filter array 21, as shown in FIG. 5, color transmitting filters 21R, 21G and 21B transmitting respectively the lights of the respective wavelengths (colors) of the three primary colors of red(R), green(G) and blue(B) are arrayed in the form of a mosaic or stripes so as to be opposed to the respective light receiving elements of the above mentioned solid state imaging device 22.

As shown in FIGS. 2 to 4, the above mentioned solid state imaging device 22 is provided with a base 23 made of ceramics or glass epoxy and a rectangular solid state imaging chip 24 secured on the base 23. The solid state imaging chip 24 is provided with a substantially square image area 25 and chip side bonding pads 26. In this embodiment, the above mentioned chip side bonding pads 26 are provided in a row on one side of the above mentioned image area. The pitch of these chip side bonding pads 26 is, for example, 0.2 mm.

On the other hand, as shown in FIG. 2, the above mentioned base 23 is formed to be protruded on the above mentioned chip side bonding pad 26 side in a space formed between a tip inside diameter 100 and a later decribed light guide 38 which is one of the contents of the endoscope and base side bonding pads 27 are provided on the protruded part 23a.

In this embodiment, these base side bonding pads 27 are arranged in the form of groups, for example, in a plurality of rows and at a high density. As shown in FIG. 3, a base side bonding pad 27 is formed to be thick in the part projecting above the above mentioned base 23 but thin in the part passing through the above mentioned base 23. The diameter of the thick part of the base side bonding pad 27 is, for example, 0.4 mm. and the pitch is, for example, 0.6 mm. Also, in this embodiment, the heights of the parts projecting above the base 23 of the above mentioned base side bonding pads are different. These base side bonding pads 27 and the above mentioned chip side bonding pads 26 are connected respectively with each other through bonding wires 28. In this embodiment, as shown in FIG. 3, these bonding wires 28 are provided to be different in the heights WH above the surface of the solid state imaging chip 24 so as not to contact each other. Further, in this embodiment, as shown in FIG. 2, some of the bonding wires intersect three-dimensionally with each other. The above mentioned chip side bonding pads 26, base side bonding pads 27 and bonding wires 28 are sealed with a sealing resin 29.

The thin part of the above mentioned base side bonding pad 27 is passed through the base 23, is then properly bent and is extended out as a lead foot 31 in a position proper for substrates 30 arranged in the rear of the solid state imaging device 22. The diameter of the lead foot 31 is, for example, 0.25 mm. In this embodiment, a plurality of the above mentioned substrates 30, for example, two are provided. Each substrate 30 is fitted with electronic parts forming an amplifying circuit or the like of the above mentioned solid state imaging device 22 such as transistors and IC's not illustrated. Also, the above mentioned lead feet 31 are different in length so as to be easy to fit to the substrate 30. These lead feet 31 are reinforced in the root parts with a sealing resin 32. A signal line 33 is connected to the above mentioned substrate 30. The signal line 33 is inserted through the above mentioned insertable part 2 and is connected to the connector receiver 4 of the above mentioned operating part 3.

A forceps mouthpiece 34 is fitted in the above mentioned forceps channel through hole 17. A forceps channel tube 36 forming a forceps channel 35 is connected to the rear end of the forceps mouthpiece 34. The forceps channel tube 36 is inserted through the above mentioned insertable part 2 and is connected to the above mentioned inserting port 12.

A light distributing lens system, not illustrated, is fitted in an illuminating through hole which is also not illustrated. A light guide 38, coated with a light guide tube 37, is connected to the rear end of the light distributing lens system. The light guide 38 is inserted through the above mentioned insertable part 2 and is connected to the connector receiver 4 of the above mentioned operating part 3.

The cable 6, connected to the above mentioned connector receiver 4 through the connector 5, is provided with a cable transmitting a signal from the above mentioned signal line 33 to the controlling device 7 and a light guide transmitting a light from the light source device within the controlling device 7 to the above mentioned light guide 38.

An air and water feeding nozzle, not illustrated, is fitted to an air and water feeding channel through a hole which is not illustrated. An air and water feeding tube 40, forming an air and water feeding channel 39, is connected to the air and water feeding nozzle. The air and water feeding tube 40 is inserted through the above mentioned insertable part 2 and is connected to an air and water feeding port, not illustrated, provided in the above mentioned operating part 3.

As shown in FIGS. 2 and 4, the above mentioned insertable part 2 has a soft tube 41 through which the above mentioned signal line 33, forceps channel 35, light guide 38 and air and water feeding channel 39 are inserted. The soft tube 41 is connected at the front end to the rear end of the above mentioned tip body 15.

In this embodiment, as shown in FIG. 2, the base 23 of the above mentioned solid state imaging device 22 is formed so that the protruded part 23a may be arranged in a space produced in case the solid state imaging chip 24 of the above mentioned solid state imaging device 22, forceps channel 35, light guide 38 and air and water feeding channel 39 are arranged within the tip 9 of the above mentioned insertable part 2.

As shown in FIG. 5, in the case of a simultaneous system, a light source device 51 provided within the above mentioned controlling device 7 is provided, for example, with an illuminating lamp 52. An illuminating light of the illuminating lamp 52 is reflected and condensed by a reflector 53. The light is corrected to be of standard or nearly ideal spectral characteristics by a spectral characteristic correcting filter 54 and enters a light guide 55 within the above mentioned cable. The illuminating light is projected out of the tip of a light distributing lens system 56 through the above mentioned cable 6, light guide 38 and light distributing lens system 56 to illuminate an object to be imaged.

The reflected light from the above mentioned object to be imaged passes through the objective system 19 and color filter array 21 and is received by the image area 25 of the above mentioned solid state imaging device 22. The signals corresponding to the respective picture elements of the solid state imaging device 22 are read out through an output register by clock signals formed in the driver circuit of a driver preamplifier 58 on the basis of the standard signal of a standard oscillator 57. The picture element signal becomes a picture element signal of any of the three primary colors in response to the array of the respective color transmitting filters 21R, 21G and 21B of the color filter array 21. The picture element signal is amplified by the preamplifying part of the above mentioned driver preamplifier 21 and is then taken into red, green and blue sample holding circuits 60R, 60G and 60B within a video processing part 59 within the controlling device 7. The above mentioned sample holding circuits 60R, 60G and 60B are to take in the above mentioned picture element signal as respective color signals R, G and B separated into respective colors by sampling pulses output from a sampling pulse generator 61 at a timing synchronized with the picture element signal read out on the basis of the standard oscillator 57. The above mentioned respective color signals R, G and B are output to the color CRT monitor 8 to color-display the object.

Thus, in this embodiment, the base side bonding pads 27 are compactly arranged in groups in a space enclosed with the tip inside diameter 100, contents and image area 25. Further, the base side bonding pads 27 are arranged in a plurality of rows and the above mentioned base side bonding pads 27 and bonding wires 28 are provided which different heights so that the bonding wires 28 may not contact each other. Therefore, these base side bonding pads 27 can be arranged in a part desirable to the layout and can be collected in a high density. As a result, the solid state imaging device 22 can be made small or formed to be desirable to make the insertable part thin in the layout and the insertable part 2 can be made thin.

Now, the layout of the contents (what current or signal flows through the respective chip side bonding pads 26) of the above mentioned chip side bonding pads 26 is restricted in the design of the semiconductor circuit in the solid state imaging chip 24. The layout of the contents of the above mentioned base side bonding pads 27 is restricted by the layout of the contents of respective leads of electronic parts forming the electric circuit of the driver preamplifier 58 or the like connected with the solid state imaging device 22 and the layout of the contents of the land provided on the substrate 30 fitted with such leads. According to this embodiment, as the above mentioned base side bonding pads 27 can be freely laid out, the restriction on the above mentioned chip side bonding pads 26 and the restriction on the above mentioned base side bonding pads 27 are compatible with each other. As a result, the solid state imaging device 22 and substrate 30 can be designed to be smallest. In this respect, too, the insertable part 2 can be made small in diameter.

In this embodiment, the base side bonding pads 27 are arranged in a plurality of rows but need not be in rows and may be arranged at random in groups.

In this embodiment, the chip side bonding pads 26 are provided in one row but may be in a plurality of rows. Thus, in case the chip side bonding pads 26 are not provided on a plurality of sides of the image area 25 but are provided in a plurality of rows on one side of the image area, it will be desirable to the layout to make the insertable part small in diameter.

In case the hollow space within the tip of the insertable part 2 can be effectively utilized, the above mentioned chip side bonding pads 26 and base side bonding pads 27 may be arranged on a plurality of sides of the image area.

The above mentioned base side bonding pads 27 may be the same in height and only the bonding wires 28 may be different in height.

Figure 6:
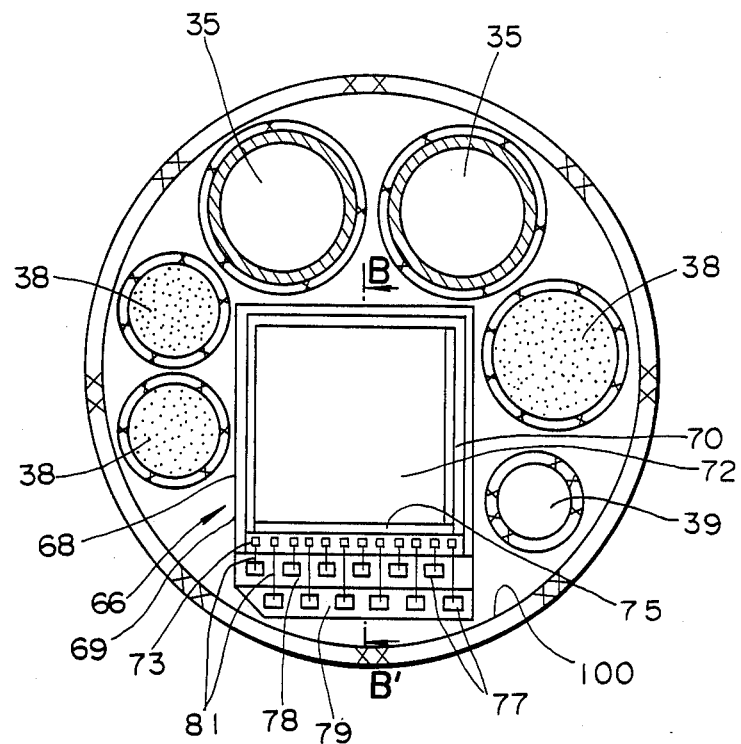
FIGS. 6 and 7 relate to the second embodiment of the present invention.
Figure 7:
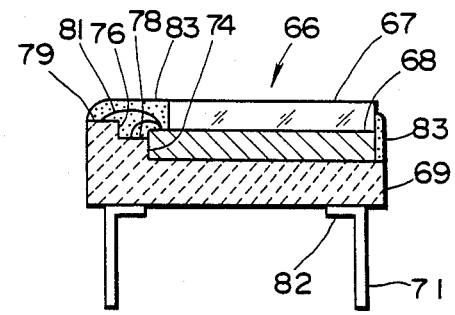

FIGS. 6 and 7 relate to the second embodiment of the present invention. FIG. 6 is a cross-sectioned view of a tip of the insertable part of an electronic endoscope. FIG. 7 is a sectioned view in the direction B—B' in FIG. 6.

This embodiment is of an electronic endoscope wherein two forceps channels are arranged and many light guides are arranged so that the shadows of treating tools such as forceps may not have a negative influence.

A solid state imaging device 66 is provided in a space enclosed with the tip inside diameter 100, forceps channels 35 and contents such as the light guide 38.

Chip side bonding pads 73 are provided in a row on one side of an image area 72 on the tip inside diameter 100 side and base side bonding pads 77 are provided in two rows and the corner of the outside row of the base side bonding pads 77 is chamfered.

The solid state imaging device 66 is formed of a color filter array 67, solid state imaging chip 68, base 69 and lead member 71.

On the above mentioned solid state imaging chip 68, the square image area 72 is formed in the central part except on the peripheral sides and, for example, 12 chip side bonding pads 73 are provided in one row along one side on one somewhat widened side on the periphery of the image area 72.

A main optical black row 70, for detecting a black level, is provided on one of the four peripheral sides of the image area 72. A horizontal shift register 75, connected to the respective picture elements of the solid state imaging chip 68, is provided on another side. The color filter array 67, formed by arranging in the form of a mosaic or stripes color transmitting filters 67R, 67G and 67B transmitting respectively the lights of the respective wavelengths (colors) of the three primary colors of red(R), green(G), and blue(B) so as to be opposed to the respective light receiving elements of the above mentioned solid state imaging chip 68, is provided to overlap on the above mentioned image area 72.

As in FIG. 7, the above mentioned base 69 is formed as a rectangular plate made of material such as, for example, a multilayer ceramic substrate and having three kinds of thickness by steps 74 and 76.

The front surface of the thinnest part formed by the step 74 has an area somewhat larger than the above mentioned solid state imaging chip 68 and the solid state imaging chip 68 is secured so as to be in contact on the end surface on the side having the above mentioned chip side bonding pads 73 with the above mentioned step 74.

The part exposed out of the solid state imaging chip 68 of the front surface of the above mentioned base 69 is formed to be stepped so that the edge side may be made thicker by the above mentioned step 76.

The low bonding pad part 78, which is the front surface of the base 69 located between the above mentioned steps 74 and 76, is somewhat lower than the imaging surface of the above mentioned solid state imaging chip 68. The high bonding pad part 79 which is the front surface of the base 69 located between the above mentioned step 76 and the end surface of the base 69, is formed to be somewhat higher than the imaging surface of the above mentioned solid state imaging chip 68.

On each of the above mentioned low bonding pad part 78 and high bonding pad part 79, for example, six base side bonding pads 77 are provided in one row so as to correspond to the above mentioned chip side bonding pads 73 and, as a whole, the base side bonding pads 77 form groups.

As in FIG. 6, the base side bonding pads 77 provided on the above mentioned low bonding pad part 78 and the base side bonding pads 77 provided on the high bonding pad part 79 are alternately connected with the chip side bonding pads 73 through bonding wires 81 so as to be parallel with each other without intersecting.

The above mentioned base side bonding pads 77 are connected to a flat land, not illustrated, provided on the back surface of the base 69 through internal wirings through the base 69. A flange 82, provided at one end of the above mentioned lead member 71, is secured on the end surface to the above mentioned flat land.

The above mentioned chip side bonding pads 73, base side bonding pads 77 and bonding wires 81 together with the front surface of the base 69, slightly expose out of the end surface of the solid state imaging chip 68, are sealed with a sealing resin 83.

In this embodiment, the corner of the base side bonding pads 77 on the tip inside diameter 100 side is chamfered and the front surface side of the base 69 is formed to be stepped to provide the base side bonding pads 77 to obtain the same effect as in the first embodiment.

In this embodiment, the bonding pad part provided on the base 69 is made in two steps but is not so restricted and may be in three or more steps.

The present invention can be applied not only to the simultaneous system in which the color filters are arranged in front of the solid state imaging devices 22 and 66 but also to the field sequential system in which the illuminating light is switched in sequence to red, green and blue.

As mentioned above, according to the present invention, the space within the endoscope tip can be most effectively utilized and the endoscope can be made small in the diameter.

The solid state imaging device chip is hard to make in any other form than rectangular but the base can be made in any form and therefore may be in any form in response to the feature (for example, one or two forceps channels) of each kind of electronic endoscope.

When the solid state imaging device is provided in a space enclosed with the tip inside diameter and contents and the base side bonding pads are arranged compactly in groups in a space enclosed with the tip inside diameter, contents and image area, the tip inside diameter can be made smallest. In such a case, if the heights of the base side bonding pads and the heights of the bonding wires are made a plurality of heights, the bonding wires can be prevented from interfering with each other and the pitch of the base side bonding pads can be made small.

The tip inside diameter is not illustrated but, correctly speaking, is the inside diameter of the first frame of the curvable part connected to the tip body 15.

It is apparent that, in this invention, working modes different in a wide range can be formed on the basis of this invention without departing from the spirit and scope of the invention. This invention is not restricted by its specific working mode except being limited by the appended claims.

What is claimed is:

1. An electronic endoscope comprising:
an operating part;
a flexible insertable part formed to have a diameter which is smaller than a diameter of the operating part;
contents of said flexible insertable part including at least a light guide arranged over an entire length within said insertable part;
a solid state imaging device provided within a tip of said insertable part, provided substantially at right angles with an axial direction of the insertable part and provided in a space enclosed with an inside diameter of the insertable part and said contents;
a solid state imaging chip forming said solid state imaging device and having an image area and chip side bonding pads provided along one side of said image area;
a base securing said solid state imaging chip;
base side bonding pads provided in groups on said base; and
bonding wires connecting said chip side bonding pads and base side bonding pads respectively with each other.

2. An electronic endoscope according to claim 1 wherein said base side bonding pads are respectively of different heights.

3. An electronic endoscope according to claim 1 wherein said solid state imaging chip has a rectangular plate-like form.

4. An electronic endoscope according to claim 1 wherein said chip side bonding pads are arranged in a row along one of four sides of said solid state imaging chip.

5. An electronic endoscope according to claim 1 wherein said base has a protruded part on which said base side bonding pads can be arranged.

6. An electronic endoscope according to claim 1 wherein said base has on a front surface a low bonding pad part and high bonding pad part which are formed like steps and on which said base side bonding pads can be arranged.

7. An electronic endoscope according to claim 1 wherein each base side bonding pad is one end surface of each lead foot passing through said base.

8. An electronic endoscope according to claim 1 wherein said base side bonding pads are provided on a low bonding pad part and a high bonding pad part.

9. An electronic endoscope according to claim 6 wherein a thickness of said low bonding part is thinner than a thickness of a base including said solid state imaging chip secured to the base.

10. An electronic endoscope according to claim 6, wherein the thickness of said high bonding part is thicker than a thickness of a base including said solid state imaging chip secured to the base.

11. An electronic endoscope according to claim 7 wherein said base side bonding pads are arranged in a plurality of rows and at a high density.

12. An electronic endoscope according to claim 7 wherein each lead foot is formed to be thick on the base side bonding pad side and thin on the back surface side.

13. An electronic endoscope according to claim 7 wherein said lead feet are secured on the base back surface by a sealing resin.

14. An electronic endoscope according to claim 7 wherein said bonding wires connected to said base side bonding pads are made to three-dimensionally intersect respectively with each other without contacting each other.

15. An electronic endoscope according to claim 8 wherein said base side bonding pads are arranged in two rows along one side of said solid state imaging chip.

16. An electronic endoscope according to claim 15 wherein said base side bonding pads are arranged alternately with each other.

17. An electronic endoscope according to claim 15 wherein said bonding wires connected to said base side bonding pads are parallel with each other.

18. An electronic endoscope according to claim 1 wherein the base is chamfered in a corner part positioned on the insertable part tip inside diameter side.

* * * * *